United States Patent
Burgo et al.

(10) Patent No.: US 9,662,288 B2
(45) Date of Patent: May 30, 2017

(54) HAIR CONDITIONING COSMETIC COMPOSITIONS CONTAINING A MIXTURE OF AMIDOAMINES

(71) Applicant: Inolex Investment Corporation, Wilmington, DE (US)

(72) Inventors: Rocco Burgo, Mullica Hill, NJ (US); Jeffrey Parker, New Hope, PA (US)

(73) Assignee: Inolex Investment Corporation, Wilmington, DE (US)

( * ) Notice: Subject to any disclaimer, the term of this patent is extended or adjusted under 35 U.S.C. 154(b) by 0 days.

(21) Appl. No.: 14/336,527

(22) Filed: Jul. 21, 2014

(65) Prior Publication Data

US 2014/0328784 A1 Nov. 6, 2014

Related U.S. Application Data

(63) Continuation of application No. 11/784,899, filed on Apr. 10, 2007, now abandoned.

(60) Provisional application No. 60/790,658, filed on Apr. 10, 2006.

(51) Int. Cl.
*A61K 8/42* (2006.01)
*A61Q 5/12* (2006.01)

(52) U.S. Cl.
CPC ............... *A61K 8/42* (2013.01); *A61Q 5/12* (2013.01); *A61K 2800/59* (2013.01); *A61K 2800/592* (2013.01)

(58) Field of Classification Search
CPC .......... A61K 2800/59; A61K 2800/592; A61K 8/42; A61Q 5/12
See application file for complete search history.

(56) References Cited

U.S. PATENT DOCUMENTS

| | | | |
|---|---|---|---|
| 4,954,335 A | 9/1990 | Janchipraponvej | |
| 6,315,991 B1 | 11/2001 | Zofchak et al. | |
| 6,365,142 B1 | 4/2002 | Tamura | |
| 6,592,856 B2 | 7/2003 | Giles et al. | |
| 6,979,439 B1 | 12/2005 | Sakai et al. | |
| 7,147,843 B2 * | 12/2006 | Yoshida et al. | 424/70.9 |
| 2003/0012761 A1 | 1/2003 | Yoshida et al. | |
| 2004/0096412 A1 | 5/2004 | Uehara et al. | |
| 2005/0232893 A1 * | 10/2005 | Kaharu et al. | 424/70.27 |

FOREIGN PATENT DOCUMENTS

| | | |
|---|---|---|
| EP | 1714677 A1 | 10/2006 |
| EP | 1808157 A1 | 7/2007 |
| JP | 2002-114648 A | 4/2002 |
| WO | 02/00179 A1 | 1/2002 |

(Continued)

OTHER PUBLICATIONS

Extended European Search Report and Search Opinion of Oct. 26, 2012 in Application No. 07775140.2 (8 pages).

(Continued)

*Primary Examiner* — Aradhana Sasan
(74) *Attorney, Agent, or Firm* — Flaster/Greenberg P.C.

(57) ABSTRACT

Compositions are provided and described herein which include cosmetic and hair conditioning compositions having a mixture of stearamidopropyl dimethylamine and behenamidopropyl dimethylamine. Also provided are methods for conditioning hair using such mixtures.

7 Claims, 1 Drawing Sheet

(56) References Cited

FOREIGN PATENT DOCUMENTS

WO      WO 0200179 A1 * 1/2002

OTHER PUBLICATIONS

Response to European Search Report dated May 22, 2013 in Application No. 07775140.2 (12 pages).
European Office Action of Nov. 26, 2014 in Application No. 07775140.2 (8 pages).
Response to Office Action dated Jun. 5, 2015 in Application No. 07775140.2 (5 pages).
European Office Action of Jan. 12, 2016 in Application No. 07775140.2 (9 pages).
Response to European Office Action dated Jul. 22, 2016 in Application No. 07775140.2 (3 pages).

* cited by examiner

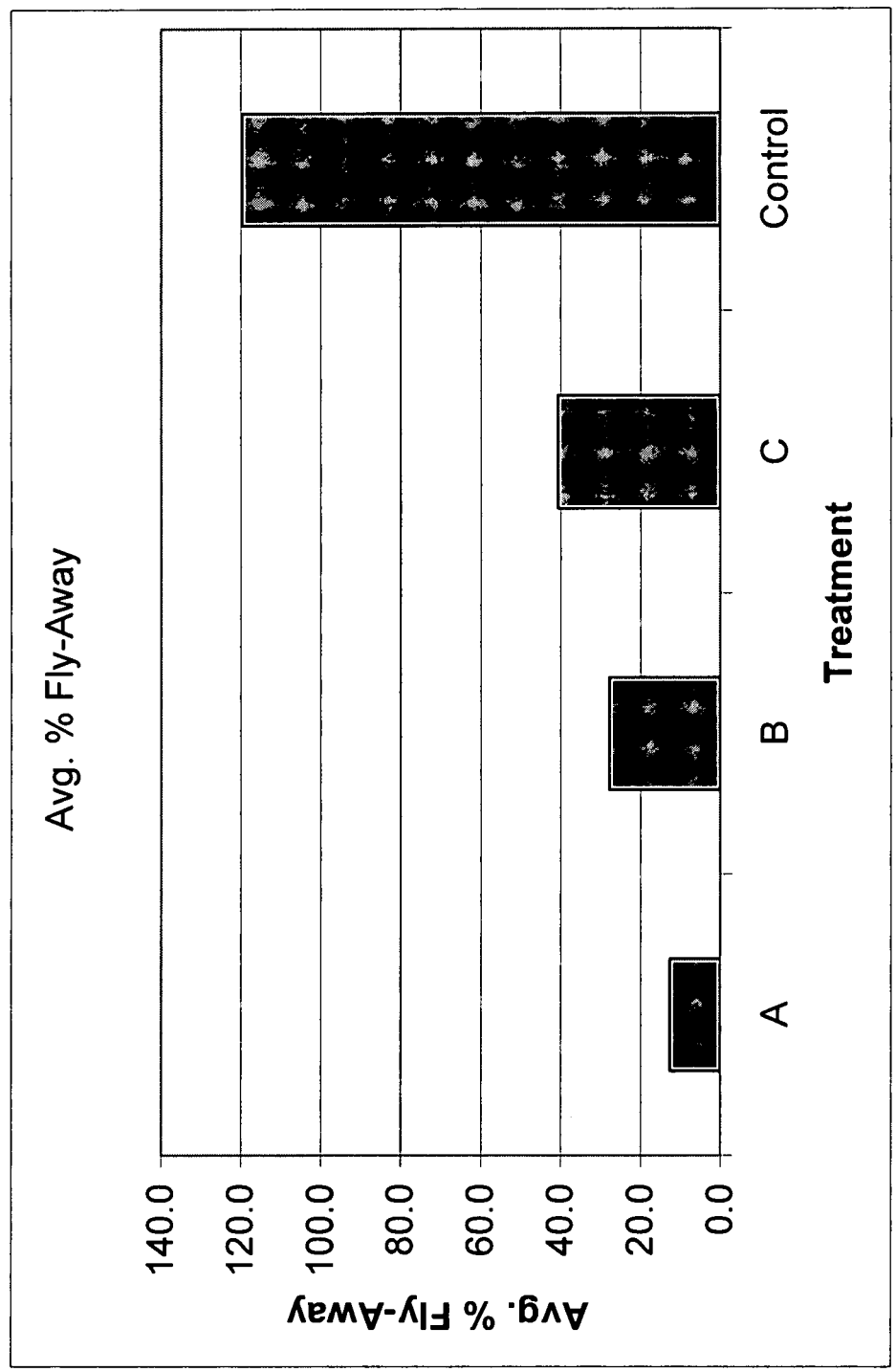

HAIR CONDITIONING COSMETIC COMPOSITIONS CONTAINING A MIXTURE OF AMIDOAMINES

CROSS-REFERENCE TO RELATED APPLICATIONS

This application is a continuation of prior-filed, copending U.S. patent applications Ser. No. 11//784,899, filed Apr. 10, 2007, which in turn claims priority to and the benefit under 35 U.S.C. §119(e) to U.S. Provisional Patent Application No. 60/790,658, filed Apr. 10, 2006, the entire disclosures of each of which are incorporated herein by reference in their entireties.

BACKGROUND OF THE INVENTION

Hair conditioners are utilized globally to improve the texture and appearance of human hair. These formulations may confer specific benefits that are broadly defined as hair manageability. More specifically, hair manageability may be thought of as a combination of benefits such as reduction and/or removal of static charge, detangling, strengthening, split-end removal, shine improvement, thickening, fragrance delivery, moisturization, lubrication and other properties that generally result in the perception of repair of damaged hair and of enhanced beautification.

Compositions have been discovered that provide conditioning benefits simultaneously with cleansing and are known in the field as "two-in-one shampoos." Although these have gained significant popularity, the predominant proportion of hair conditioning products are applied after shampooing, and may be designed to be rinsed off ("rinse-off") or left on ("leave-on") the hair. A conditioner that is used after shampooing in a separate step is called a conventional conditioner.

Conventional conditioner formulations are typically made in the form of oil-in-water (O/W) emulsions. Although the O/W emulsion is the preferred type, other product forms such as gels, creams, solutions, pastes, sprays, and mousses are also provided.

One property of conditioners that is preferred among consumers is for the viscosity of the product to be sufficiently high such that upon application, the product provides a feeling of creaminess and cushion between the hair and the hand. Another property that is preferred is that lubricity is provided by the conditioner, and during rinse-off, this lubricity is perceived as immediate improvement in the softness and smoothness of the hair. Yet another property that is preferred is that the hair surface be revitalized after the hair has dried out. This can be demonstrated by the ease with which combing or brushing is accomplished, and by visual characteristics such as shine. Yet another property that is preferred is that the hair maintains the shape and texture desired by the consumer just after drying, brushing and/or combing. Terms such as "frizziness" and "flyaway" are used in the field to describe loss of shape and/or texture. These terms have a negative connotation, and are generally associated with a lack of conditioning of the hair.

Cationic materials have been found to be particularly effective for controlling viscosity, providing lubrication during rinse off, reducing wet and dry combing force, improving shine, and improving the texture and the shape of the hair. Hair consists predominantly of keratin, and its surface is rich in negatively charged amino acids. Cationic materials will thus bind to the hair by electrostatic attraction, and will not be rinsed out completely. Particularly effective cationic materials are those in which the cationic site is on one end of the molecule, with the remainder of the molecule consisting of a long hydrophobic moiety. Cationic materials of this type can create a temporary new hair surface in which the topography is filled with organic material. The smoother hair surface reduces friction between the hair surface and hair styling implements such as combs and brushes, as well as the hand. Additionally, the smoother surface will tend to improve the ability of light to reflect off of the hair that results in improved shininess. Although certain cationic materials are known to provide such benefits, there is an ongoing need for materials that improve upon them.

A particularly useful class of cationic materials that may provide the aforementioned benefits are the amidoamines. Amidoamines are derived from the reaction of fatty acids with polyamines that contain at least one tertiary amine group. Stearamidopropyl dimethylamine (Lexamine® S-13, Inolex Chemical Company, Philadelphia, Pa., USA) is the reaction product of stearic acid (linear, C-18) with dimethylaminopropylamine. Behenamidopropyl dimethylamine (Lexamine® B-13, Inolex Chemical Company, Philadelphia, Pa., USA) is the reaction product of behenic acid (linear, C-22) with dimethylaminopropylamine. Stearamidoethyl diethylamine (Lexamine® 22, Inolex Chemical Company, Philadelphia, Pa., USA) is the reaction product of stearic acid (linear, C-18) with diethylaminoethylamine. Each of these products has been used successfully for many years alone or in combination with other types of conditioning ingredients in hair conditioning compositions.

Commercial forms of behenic acid are known which are derived from Menhaden (fish) oil. One such product was available from Witco under the name Hystrene® 9022. The applicants are unaware of the actual behenic content. Applicants are also aware of a product which has a behenic amidoamine content of about 60-65% and a stearic amidoamine content of about 20-25%, such that the maximum stearic/behenic ratio is about 0.417. To the best of applicants' knowledge all such products were derived from the reaction of dimethylaminopropylamine with fatty acids.

Representative patents directed to use of amidoamines in hair formulations include U.S. Pat. No. 4,954,335, which describes the usefulness of amidoamines in the formulation of clear hair conditioners. U.S. Pat. No. 6,365,142 also discloses the use of amidoamines in combination with other ingredients to form a hair conditioner. U.S. Pat. No. 6,979,439 discloses the use of amidoamines in anti-dandruff preparations. Although the prior art discloses the possible use of amidoamines in combination in hair care formulations, there have been no disclosures that suggest a particular advantage of any such combinations. Additionally, applicants are unaware of a particular theory that has been applied to account for or predict any a potential relationship between chemical structure and physical properties that would serve as a basis for one skilled in the art to predict the benefits or outcome of particular combinations of such compounds other than what would be expected in terms of general additive contributions of individual components.

BRIEF SUMMARY OF THE INVENTION

The invention includes a composition, comprising a mixture of stearamidopropyl dimethylamine and behenamidopropyl dimethylamine, wherein a weight ratio of stearamidopropyl dimethylamine to behenamidopropyl dimethylamine is about 0.60:1.00 to about 0.85:1.00.

The invention also includes a composition, comprising a mixture of stearamidopropyl dimethylamine and behenamidopropyl dimethylamine, wherein the stearamidopropyl dimethylamine and the behenamidopropyl dimethylamine are reaction products of hydrogenated high erucic acid rapeseed oil with dimethylaminopropylamine.

A hair conditioning composition is also included herein which comprises a mixture of stearamidopropyl dimethylamine and behenamidopropyl dimethylamine, wherein a weight ratio of stearamidopropyl dimethylamine to behenamidopropyl dimethylamine is about 0.60:1.00 to about 0.85:1.00.

The invention further includes a method of conditioning hair, comprising applying a composition topically to the hair, wherein the composition comprises a mixture of stearamidopropyl dimethylamine and behenamidopropyl dimethylamine present in a ratio of stearamidopropyl dimethylamine to behenamidopropyl dimethylamine is about 0.60:1.00 to about 0.85:1.00.

BRIEF DESCRIPTION OF THE SEVERAL VIEWS OF THE DRAWING(S)

The foregoing summary, as well as the following detailed description of preferred embodiments of the invention, will be better understood when read in conjunction with the appended drawing. For the purpose of illustrating the invention, there is shown in the drawing results from an embodiment in Example 1 that includes embodiments which are presently preferred. It should be understood, however, that the invention is not limited to the precise arrangements and instrumentalities shown. In the drawings:

FIG. 1 is a graphical representation of the average percentage flyaway hair for various samples in Example 1.

DETAILED DESCRIPTION OF THE INVENTION

This invention relates to a method of preparing compositions, preferably cosmetic compositions, and more preferably hair conditioning compositions including as an active component a preferred mixture of amidoamines. The preferred amidoamines used in the compositions of the present invention are stearamidopropyl dimethylamine and behenamidopropyl dimethylamine. The mixture of these two amidoamines provides enhanced conditioning benefits when applied to the hair. Preferably, the two amidoamines are present in a ratio of about 0.60:1.00 to about 0.85:1.00 and, most preferably are also derived from rapeseed oil as described further herein.

More particularly, the invention relates to mixtures of amidoamines, particularly a mixture of amidoamines, which may be derived from reaction of hydrogenated high erucic acid rapeseed oil (Hyd. HEAR oil) with dimethylaminopropylamine.

Rapeseed oil (Hyd. HEAR oil) may be derived from various sources, but is preferably, although not exclusively derived from Rapeseed in the family Brassicaceae. Preferred rapeseed oil for use in the present invention includes rapeseed oils derived from botanical sources including, for example, *B. napobrassica, B. napus, B. rapa, B. campestris, B. juncea* and/or *Sinapsis alba* or various combinations and derivatives thereof. It is a preferred for the purpose of the invention that these oils be hydrogenated, preferably to an iodine value of less than 20.0 cg $I_2$/g, and more preferably to an iodine value of less than about 5.0 cg $I_2$/g, and most preferably to an iodine value of less than 1.0 cg $I_2$/g, prior to their being used.

The rapeseed oil is preferably reacted with a dialkylaminoalkylamine to form the amidoamine mixtures herein. Preferred dialkylaminoalkylamines include dimethylaminopropylamine, diethylaminoethylamine, dimethylaminoethylamine, diethylaminopropylamine, and the like. Most preferred is dimethylaminopropylamine, however, it should be understood based on this disclosure that other such compounds may be useful as well. Thus, the preferred reaction occurs through the transamidation of hydrogenated rapeseed oil, in which a dialkylaminoalkylamine is reacted with hydrogenated rapeseed oil to yield amidoamine and about 9% glycerine that remains in the final reaction product.

Upon investigation of amidoamines for certain hair conditioning properties, applicants have surprisingly discovered that certain amidoamines mixtures, preferably when utilized in defined ratios provide unexpectedly improved results.

The resulting amidoamine mixture formed by the reaction of rapeseed oil and dialkylaminoalkylamine has beneficial properties for various compositions, including cosmetic compositions such as hair conditioning compositions. The preferred amidoamine reaction products produced from the above-noted reaction include certain preferred combinations of stearamidopropyl dimethylamine and behenamidopropyl dimethylamine or their variations and derivatives (depending on the starting materials used). Such combinations provide unique properties.

It is preferred that such amidoamines are used in mixtures of at least two such compounds. In such mixtures, it is preferred that there is a primary component and that the weight ratio of a secondary amidoamine to a primary amidoamine is about 0.05:1.00 to about 0.95:1.00, with a combined value of secondary amidoamines to primary amidoamine of about 0.25:1.00 to about 0.95:1.00. Most preferably the invention includes mixtures of stearamidopropyl dimethylamine and behenamidopropyl dimethylamine in a weight ratio of about 0.60:1.00 to about 0.85:1.00 stearamidopropyl dimethylamine to behenamidopropyl dimethylamine. Such mixtures provide improvements in certain properties that are related to performance in hair conditioners that are generally above and beyond those that would be expected by the mere additive contributions of each compound.

It is further preferred to use in conditioning formulations combinations of amidoamines including a mixture having stearamidopropyl dimethylamine and behenamidopropyl dimethylamine, wherein the mixture is prepared by reacting Hyd. HEAR oil with dimethylaminopropylamine. Such mixtures contribute properties such as the improved performance in reducing flyaway hair, which corresponds to improved performance when used in hair conditioner formulations.

In the preferred compositions according to the invention derived from Hyd. HEAR oil, the preferred weight ratio of stearamidopropyl dimethylamine to behenamidopropyl dimethylamine preferably corresponds to that which is derived from the weight ratio of stearic acid to behenic acid naturally found in Hyd. HEAR oil. This ratio can vary according to the particular genus or species of botanical in which the rapeseed oil is derived, but generally falls within the preferred weight ratio noted above of about 0.60:1.00 to about 0.85:1.00.

Alternatively, the composition according to the invention may be prepared by the reaction of stearic acid, obtained from any natural or synthetic source, and behenic acid, obtained from any natural or synthetic source, with dimethylaminopropylamine. However, it is preferred that for such reactions, the ratio of stearic acid to behenic acid in the parent fatty acid mixture falls within the range of about 0.60:1.00 to about 0.85:1.00.

A further aspect of the invention is a method of using the compositions of the present invention in a hair conditioner composition. The hair conditioner composition according to method of the invention is preferably in the form of an oil-in-water emulsion, but can also be in a form selected from the group consisting of creams, lotions, solutions, gels, pastes, mousses, sprays and combinations thereof. The proportion of the amidoamine mixture composition used in the hair condition composition is preferably from about 0.1 to about 10.0 weight percent, and more preferably from about 0.25 to about 5.0 weight percent.

While hair conditioning compositions present preferred uses of the present amidoamine compositions, it is within the scope of the invention to use such mixtures of amidoamines in other cosmetic compositions, for example, hair detergents such as shampoo, rinses, conditioning shampoos, hair lotions, hair treatments, hear creams, hair sprays, hair liquids, hair waxes, hair-styling preparations, perming liquids, hair colorants, acidic hair colorants, hair manicures, glazes, skin lotions, milky lotions, face washes, makeup removers, cleansing lotions, emollient lotions, nourishing creams, emollient creams, massage creams, cleansing creams, body shampoos, hand soaps, bar soaps, shaving creams, sunscreens, sunburn treatments, deodorants in various formulations, makeup removing gels, moisture gels, moisture essences, UV-preventing essences, shaving foams, face powders, foundations, lipsticks, blushes, eyeliners, wrinkle and anti-aging creams, eye shadows, eyebrow pencils, mascaras, mouthwashes, toothpastes and the like.

Any other various ordinary additives may be added to compositions according to the invention, however, it is preferred that additives not be provided which may detract from the preferred beneficial results delivered by the invention. Additives which may be used in various compositions including hair conditioners and other cosmetic formulations as those noted above include various anionic surfactants, cationic surfactants, amphoteric surfactants, nonionic surfactants, waxes, other oils and fats and derivatives thereof, fatty acid esters of varying chain lengths, synthetic oils and fats, polymers, alcohols, polyhydric alcohols, extracts useful for providing fragrance, amino acids, nucleic acids, vitamins, hydrolyzed proteins and derivatives thereof, glycerin and derivates thereof, enzymes, anti-inflammatory and other medicaments, microbiocides, antifungals, antiseptics, antioxidants, UV absorbers, dyes and pigments, sunscreen active agents, chelating agents, sweat retardants, oxidizers, pH balancing agents, moisturizers and the like approved for use in formulations for human use.

Other components, including those selected from the above components, which may be typically used in such hair conditioning compositions may also be used in preferred embodiments of hair conditioning compositions described herein and include, in addition to the preferred amidoamine mixtures of the present invention, additives such as, EDTA, glutamic acid, glycerin, panthenol, stearyl alcohol, cetyl alcohol, cyclomethicone, dimethicone, pH adjustment additives, and preferably a water base.

EXAMPLE 1

To demonstrate the new and unexpected results achieved by the present invention, model hair conditioning formulations were prepared to test for the reduction in flyaway hair. The composition of the model formulations is shown in Table 1 below:

TABLE 1

| Ingredients | % w/w |
| --- | --- |
| Deionized water | Q.S. to 100 |
| EDTA | 0.10 |
| Glutamic acid | 0.35 |
| Glycerin, 96% | 0.05 |
| Panthenol | 0.10 |
| Stearyl alcohol | 5.00 |
| Cetyl alcohol | 4.00 |
| Conditioning Amidoamine | 2.00 |
| Cyclomethicone | 2.00 |
| Dimethicone | 0.20 |
| Citric acid, 25% aq. Solution | Q.S. to 5.30 ± 0.30 |
| NaOH, 10% aq. Solution | Q.S. to 5.30 ± 0.30 |
| Total | 100.00 |

The formulations were prepared using the following procedure. Deionized water, EDTA, glutamic acid, glycerin, and panthenol were combined in a vessel with propeller agitation and heated to about 70 to about 75° C. and agitated until a uniform mixture was obtained. In a separate vessel, stearyl alcohol, cetyl alcohol, cyclomethicone, dimethicone, and the conditioning additive (amidoamine) were combined and heated to about 70 to about 75° C. and agitated until a uniform mixture was obtained. The contents of the second vessel were added to the first, and agitated at a temperature of about 70 to about 75° C. until a uniform mixture was obtained. The mixture was then homogenized for about 5 minutes at 3500 RPM. The mixture was then allowed to cool with gentle agitation to about 40° C. to about 45° C. The pH of the mixture was then adjusted to about 4.9 to about 5.6 with citric acid and/or sodium hydroxide solution. The mixture was then allowed to cool to about 15° C. to about 25° C. with gentle agitation. Agitation was then stopped, and the completed conditioner formulation was poured off to containers.

Test formulations were prepared using the above procedure that contained the following concentrations of conditioning additive as set forth in Table 2:

TABLE 2

| Test Formulation Identifier | Stearamidopropyl Dimethylamine, weight ratio | Behenamidopropyl Dimethylamine, weight ratio |
| --- | --- | --- |
| A | 0.7 | 1.0 |
| B | 0.0 | 1.0 |
| C | 1.0 | 0.0 |
| Control | 0.0 | 0.0 |

Flyaway properties of the test formulation were determined using the following procedure. Five hair tresses were prepared for each formulation by first washing in sodium lauryl ether sulfate solution. Each of the tresses were then combed as necessary to remove any knots or tangles, then allowed to dry thoroughly. The conditioning formulation was then applied to each tress and massaged in thoroughly, then rinsed with water. After treatment, each tress was then again combed to remove any knots or tangles, following which it was allowed to dry for about five hours. Each tress was then transferred to a controlled humidity environment and allowed to acclimate for about 30 minutes. The width of each tress was measured. Each tress was then combed twenty times after which the tress was again measured. The percentage increase in the width of each tress after combing is directly related to the presence of fly-away hair, and is directly related to the conditioning benefit provided by the conditioner formulation with lower values being better. The following data in Table 3 were obtained.

TABLE 3

| Treatment | Tress | Pre-Comb width (cm) | Post-Comb width (cm) | Difference (cm) | % Fly Away |
|---|---|---|---|---|---|
| Formula A | A1 | 4.1 | 4.4 | 0.3 | 7.3 |
| | A2 | 4.0 | 4.5 | 0.5 | 12.5 |
| | A3 | 4.6 | 5.6 | 1.0 | 21.7 |
| | A4 | 4.0 | 4.4 | 0.4 | 10.0 |
| | A5 | 4.3 | 4.8 | 0.5 | 11.6 |
| Average | | 4.2 | 4.7 | 0.5 | 12.6 |
| Formula B | B1 | 3.4 | 4.8 | 1.4 | 41.2 |
| | B2 | 3.6 | 5.0 | 1.4 | 38.9 |
| | B3 | 4.1 | 4.4 | 0.3 | 7.3 |
| | B4 | 3.0 | 3.7 | 0.7 | 23.3 |
| | B5 | 2.5 | 3.2 | 0.7 | 28.0 |
| Average | | 3.3 | 4.2 | 0.9 | 27.7 |
| Formula C | C1 | 3.5 | 4.3 | 0.8 | 22.9 |
| | C2 | 3.1 | 4.1 | 1.0 | 32.3 |
| | C3 | 3.9 | 4.9 | 1.0 | 25.6 |
| | C4 | 3.7 | 4.8 | 1.1 | 29.7 |
| | C5 | 2.9 | 5.6 | 2.7 | 93.1 |
| Average | | 3.4 | 4.7 | 1.3 | 40.7 |
| Control | CTRL-1 | 4.8 | 12.2 | 7.4 | 154.2 |
| | CTRL-2 | 4.1 | 8.9 | 4.8 | 117.1 |
| | CTRL-3 | 4.6 | 10.1 | 5.5 | 119.6 |
| | CTRL-4 | 6.1 | 14.0 | 7.9 | 129.5 |
| | CTRL-5 | 4.6 | 8.2 | 3.6 | 78.3 |
| Average | | 4.8 | 10.7 | 5.8 | 119.7 |

The results indicated in Table 3 and the chart in FIG. 1 illustrate the results obtained for each of the test formulations. The results indicate that Formula A comprising the mixture of amidoamines had lower percentage fly-away then either of Formula B or Formula C, which represent the amidoamines used separately, and illustrates the improvement obtained when mixing the amidoamines in accordance with the invention.

EXAMPLE 2

To further demonstrate the invention, an amidoamine was prepared from Hyd. HEAR oil using the following procedure. Dimethylaminopropylamine and Hyd. HEAR oil (Erucical H-103, Lambent Technologies, Gurnee, Ill., USA) were charged to a stirred batch reactor in a molar ratio of 2.0:1.4 and heated with inert gas sparging to about 120 to about 200° C. The mixture was held for about eight hours under this condition. Excess dimethylaminopropylamine was then removed by allowing the mixture to cool to about 140° C., and then by applying vacuum of about 750 to about 755 mm, and by steam stripping. The resulting amidoamine product was then cooled and poured off to chilled metal pans, allowed to solidify, and was then broken up into flakes. The flakes were a pale yellow, waxy consistency. Color of the product was tested using AOCS (American Oil Chemists Society, Urbana, Ill., USA) Official Method Td 1a. Acid Value was tested using ASTM (American Society of Testing and Materials International, West Conshohocken, PA, USA) Method D-974. Amine Value was tested using AOCS Tf 1b. Odor was evaluated olfactorily. Table 4 shows the results obtained.

TABLE 4

| Property | Result |
|---|---|
| Color, Gardner | 3 |
| Acid Value, mg KOH/g | 0.07 |
| Amine Value, mg KOH/g | 129.5 |
| Odor | Mild |

The amidoamine described above was tested for flyaway using the protocol described previously and in the model test formulation described previously. Table 5 shows the results obtained.

TABLE 5

| Treatment | Tress | Pre-Comb width (cm) | Post-Comb width (cm) | Difference (cm) | % Fly Away |
|---|---|---|---|---|---|
| Hyd. HEAR oil Amidoamine | 1 | 3.1 | 3.3 | 0.2 | 6.5 |
| | 2 | 4.3 | 4.3 | 0.0 | 0.0 |
| | 3 | 3.9 | 4.9 | 1.0 | 25.6 |
| | 4 | 3.9 | 4.9 | 1.0 | 25.6 |
| | 5 | 3.4 | 3.9 | 0.5 | 14.7 |
| Average | | 3.7 | 4.3 | 0.5 | 14.5 |

The percentage fly-away for the Hyd. HEAR oil amidoamine compared favorably to Formula A of Example 1, and had lower percentage fly-away than either Formula B or Formula C of Example 1, which represent the amidoamines used separately, and illustrates the improvement obtained when using the amidoamine prepared from Hyd. HEAR oil.

EXAMPLE 3

To further demonstrate the invention, the following formulations were prepared as shown in Table 6.

TABLE 6

| Ingredients | Formula A w/w % | Formula B w/w % | Formula C w/w % |
|---|---|---|---|
| Part A | | | |
| Deionized Water | 86.63 | 86.85 | 86.87 |
| EDTA | 0.10 | 0.10 | 0.10 |
| Glutamic Acid | 0.37 | 0.35 | 0.33 |
| Panthenol | 0.10 | 0.10 | 0.10 |
| Stearamidopropyl dimethylamine | 1.50 | — | — |
| Hyd. HEAR Oil Amidoamine | — | 1.50 | — |
| Behenamidopropyl dimethylamine | — | — | 1.50 |
| Part B | | | |
| Stearyl Alcohol | 5.00 | 5.00 | 5.00 |
| Cetyl Alcohol | 4.00 | 4.00 | 4.00 |
| Cyclomethicone | 2.00 | 2.00 | 2.00 |
| Dimethicone | 0.10 | 0.10 | 0.10 |
| Total | 100.00 | 100.00 | 100.00 |

The formulations were prepared as follows. Part A having deionized water, EDTA, glutamic acid, panthenol, and the amidoamine were combined in a vessel and heated with propeller agitation to about 70° C. to about 75° C. and mixed until uniform. In a separate vessel, Part B having stearyl alcohol, cetyl alcohol, dimethicone, and cyclomethicone were combined and heated with propeller agitation to about 70° C. to about 75° C. and mixed until uniform. Part B was then added to Part A, and the combination was mixed at about 70° C. to about 75° C. until uniform. The mixture was then homogenized for about 5 minutes at 3500 revolutions per minute (RPM.) The mixture was then allowed to cool with gentle agitation to about 40° C. to about 45° C. The pH of the mixture was then adjusted to about 4.9 to about 5.6 with citric acid and/or sodium hydroxide solution. The mixture was then allowed to cool to about 15° C. to about 25° C. with gentle agitation. Agitation was then stopped, and the completed conditioner formulation was poured off to containers.

The viscosity of each mixture was measured using a Brookfield RVT viscometer utilizing T spindles at 10 RPM with on helipath stand (Brookfield Engineering Laboratories Inc., Middleboro Mass.) at 20° C. The viscosity data obtained is found in Table 7.

TABLE 7

|  | Formula A | Formula B | Formula C |
|---|---|---|---|
| Viscosity@20° C., cP | 9,400 | 39,667 | 16,733 |

The results show that quite surprisingly, Formula B that was prepared from the Hyd. HEAR Oil Amidoamine developed a significantly higher viscosity in the test formulation than Formula A or Formula C, which represent the amidoamines used separately, and illustrates the improvement obtained when using the amidoamine prepared from Hyd. HEAR oil, While it has been shown and described several embodiments in accordance with the invention and use thereof, it is understood that the same is not limited thereto, but is susceptible to many changes and modifications to one possessing ordinary skill in the art, and therefore we do not wish to be limited to the details shown and described herein, but intend to cover all such modifications as are encompassed by the scope of the appended claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A mixture consisting essentially of stearamidopropyl dimethyl amine and behenamidopropyl dimethyl amine in a weight ratio of about 0.60:1.00 to about 0.85:1.00, wherein the stearamidopropyl dimethyl amine and the behenamidopropyl dimethyl amine are each reaction products of hydrogenated high erucic acid rapeseed oil with dimethytaminopropylamine, and the mixture, when applied to hair, provides improved conditioning benefits such that a hair tress treated with the mixture exhibit a reduced percentage of fly-aways.

2. The mixture of claim 1, wherein the high erucic acid rapeseed oil further comprises an oil derived from a botanical selected from the group consisting of *B. napobrassica, B. napus, B. rapa, B. campestris, B.juncea, Sinapsis alba* and combinations and derivatives thereof.

3. The mixture of claim 1, wherein the high erucic acid rapeseed oil has been hydrogenated and has an iodine value of about 20.0 cg 12/g or less.

4. The mixture of claim 1, wherein the high erucic acid rapeseed oil has an iodine value of about 5.0 cg 12/g or less.

5. The mixture of claim 1, wherein the high erucic acid rapeseed oil has an iodine value of about 1.0 cg 12/g or less.

6. A cosmetic composition containing the mixture of claim 1.

7. A hair conditioner containing the mixture of claim 1.

* * * * *